(12) United States Patent
Heismann

(10) Patent No.: US 6,826,252 B2
(45) Date of Patent: Nov. 30, 2004

(54) COMPUTED TOMOGRAPHY SCANNER AND METHOD FOR CONTROLLING THE COMPUTED TOMOGRAPHY SCANNER

(75) Inventor: Björn Heismann, Erlangen (DE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 10/454,430

(22) Filed: Jun. 4, 2003

(65) Prior Publication Data

US 2004/0013235 A1 Jan. 22, 2004

(30) Foreign Application Priority Data

Jun. 6, 2002 (DE) ......................................... 102 25 188

(51) Int. Cl.⁷ ................................................ A61B 6/03
(52) U.S. Cl. ......................... 378/16; 378/110; 378/112; 378/146
(58) Field of Search ........................... 378/4, 8, 15, 16, 378/110, 112, 146, 901

(56) References Cited

U.S. PATENT DOCUMENTS

2004/0013235 A1 * 1/2004 Heismann .................. 378/146

FOREIGN PATENT DOCUMENTS

DE    199 19 423 A 1    9/2000

* cited by examiner

Primary Examiner—David V Bruce
(74) Attorney, Agent, or Firm—Brinks Hofer Gilson & Lione

(57) ABSTRACT

A method for controlling a computed tomography scanner for producing projections of a measurement object is proposed, in which the projections are used to create images of the measurement object. The method has comprises specifying a set-point value ($\sigma_{set\text{-}point}$) for a factor ($\sigma(I)$) that is characteristic of a quality of the projections to be produced; determining an actual value of the factor ($\sigma(I)$) that is characteristic of the quality of the particular projection produced by the computed tomography scanner between the productions of successive projections; and regulating the primary intensity ($I_0$) of an X-ray source of the computed tomography scanner, between the productions of successive projections, such that the actual value for the characteristic factor ($\sigma(I)$) of each of the projections produced by the computed tomography scanner is kept at the specified set-point value ($\sigma_{set\text{-}point}$). A computed tomography scanner that is suitable for performing the method is also disclosed.

22 Claims, 2 Drawing Sheets

Figure 1:
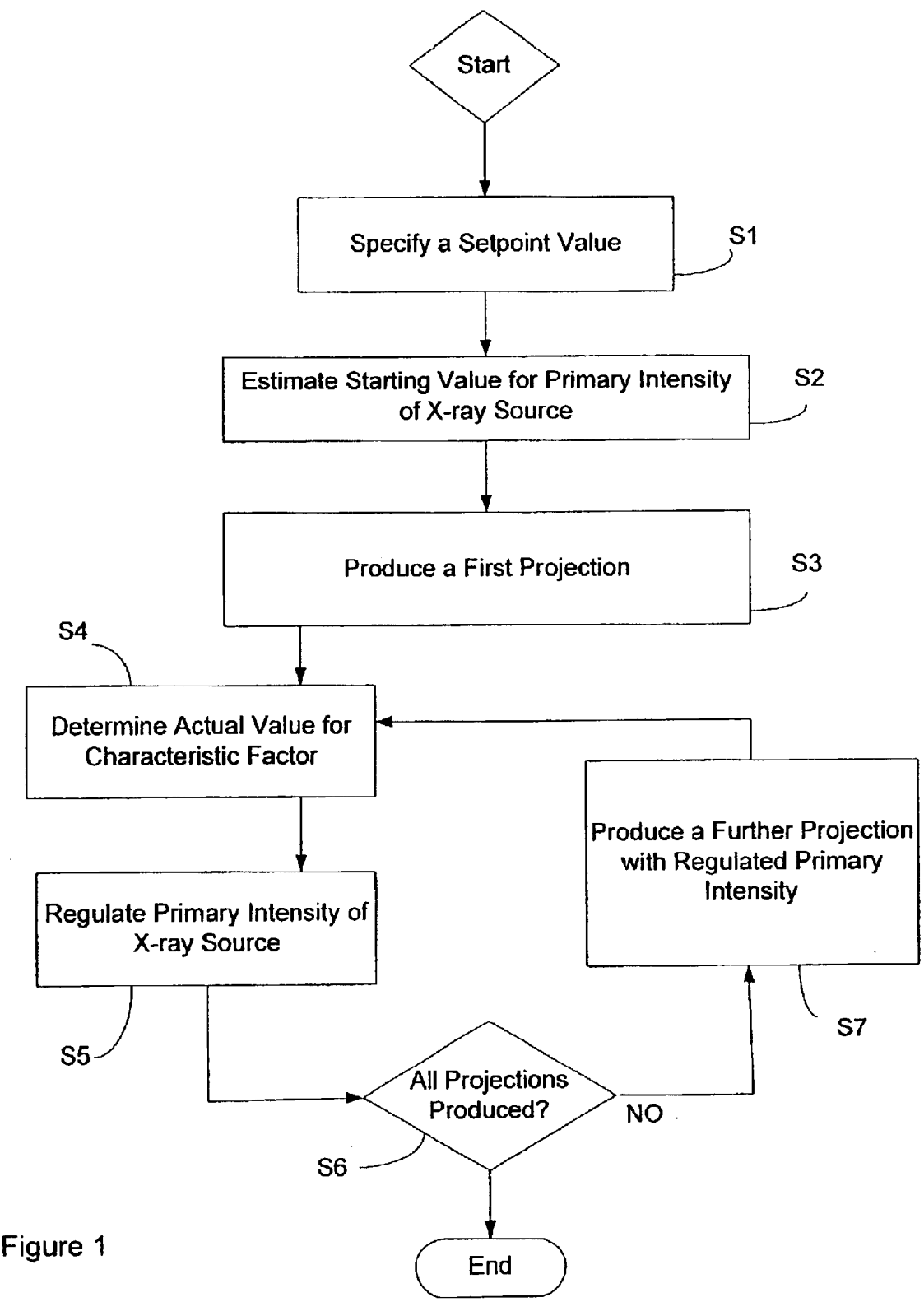

COMPUTED TOMOGRAPHY SCANNER AND METHOD FOR CONTROLLING THE COMPUTED TOMOGRAPHY SCANNER

The present invention relates to a method for controlling a computed tomography scanner, and a computed tomography scanner that is suitable for performing the claimed method.

In many problems in medicine, examinations are performed with the aid of computed tomography scanners. In some fields of mechanical engineering as well, especially materials science and aviation safety, such examinations are also used for testing purposes.

In them, X-radiation is used, which is partly capable of penetrating solid bodies, especially nonmetal bodies. As the radiation passes through a body being examined or observed, the radiation is partly absorbed, and so the intensity of the radiation is less after passing through the body being examined than before passing through it. This effect is also known as attenuation. After penetrating the body being examined, the resulting radiation can be detected, for instance by means of a semiconductor detector, and the attenuation in the radiation can thus be determined. In this way, findings about a distribution of material within the body being examined can be obtained.

A disadvantage of using X-radiation is that beyond a certain dose, it can harm biological tissue. There is accordingly a need, especially in medicine, to keep the radiation dose required for a measurement low.

In medical technology, computed tomography systems are typically used to produce pictures of slices or volumes of the human body.

A decisive factor in the diagnostic value of images obtained from projections produced by the computed tomography scanner is their image quality. The term "projection" is used to mean raw data obtained from a computed tomography scanner, from which data the desired images are then calculated. Thus, a projection as a rule includes a distribution, measured by means of a receiving unit of a computed tomography scanner, of intensity values (attenuation values) of an X-ray beam (i.e. X-radiation) emitted by an X-ray source of the computed tomography scanner.

The quality of the projections and thus the image quality of the images generated from the projections is influenced by numerous factors:

First, artifacts can occur, which can be ascribed for instance to the motion of an X-ray source and of a receiving unit of the computed tomography scanner, or to motion of the measurement object being observed while a projection is being produced or during the productions of successive projections.

Second, pixel noise in the images produced from the projections obtained from the computed tomography scanner are of definitive significance for the image quality. One important manipulated variable for pixel noise is the intensity of the radiation received. This in turn depends on the primary intensity of an X-ray beam emitted by an X-ray source of the computed tomography scanner. If the intensity of the beam, received by means of a receiving unit of the computed tomography scanner, for producing projections is high, then the pixel noise in the images generated from the projections can as a rule also be kept low.

In known computed tomography scanners, for controlling the computed tomography scanner, before images are produced, a user can specify a value for a primary intensity of the x-ray source. This primary intensity of the X-ray source is then maintained in the production of images of the body being examined. The magnitude of the primary intensity is selected such that the projections generated by means of the computed tomography scanner are expected to have adequate quality. The intention is thus to assure that even the images generated from the projections will have no more than a maximum allowable pixel noise.

Hence in the choice of the primary intensity of the X-ray source of the computed tomography scanner, the level of experience of the physician using it is of substantial significance.

Users of the known computed tomography scanners tend as a rule, in controlling the computed tomography scanner, to set a relatively high primary intensity of the X-ray source, so that a measurement object under observation, such as a patient, is exposed to a higher does of X-radiation than would actually be necessary for an image of the desired quality.

The quality of the projections obtained by means of a computed tomography scanner can also fluctuate sharply as the system moves around a patient, because of the patient geometry, since the human body overall, in contrast to its individual organs, is a non-homogeneous entity. As a result, a directional noise pattern can occur in the projections obtained and in the images generated from them.

From German Patent Disclosure DE 199 19 423 A1, a method for controlling a computed tomography scanner is known in which an aid in use is made available to a user, if before producing projections, the user has set a combination of operating parameters that are not at least inside the technological limits for the individual operating parameters. Such operating parameters of a computed tomography scanner that can be specified by a user are, besides the primary intensity of the X-ray source, the scanning time, that is, the time during which the object being examined is exposed to X-radiation for performing an examination, and the scanning length, that is, the length of the object being examined in the direction of the system axis, along which the object being examined is scanned with X-radiation for performing an examination. An operating parameter can lead to an impermissible operating state, for instance if the X-ray source is thermally overloaded, or if because of the mechanical design of the computed tomography scanner the specified scanning length cannot be scanned completely. By the known method, for at least those operating parameters, a value deviating from the pre-selected combination of operating parameters is ascertained for which the intended examination can be expected to be performed with avoidance of the impermissible operating state, without significant loss in image quality compared to the pre-selected combination of operating parameters. The changes in the operating parameters can either be set automatically or made available to the user as a suggestion. The expected quality of the projections, and thus of the images produced from the projections, is calculated using a product of the X-ray tube current and the scanning time.

Also in the method described in DE 199 19 423 A1, the primary intensity of the X-ray source is defined by a user of the computed tomography scanner. Thus in this known method for controlling a computed tomography scanner, the problems discussed above also occur, so that here as well, it is quite likely that the X-radiation dose to a body being observed will be unnecessarily high, because too high a primary intensity of the X-ray source has been selected.

It is the object of the present invention to make available a possible way of controlling a computed tomography scanner for producing projections of a measurement object, in order to generate images, that makes it possible to keep the radiation dose on the measurement object under observation as low as possible, without sacrifices in quality for the projections to be produced by the computed tomography scanner and thus for the images generated from them.

This object is attained with the characteristics of the independent claims. Refinements of the invention are defined by its dependent claims.

The object is attained by a method for controlling a computed tomography scanner for producing projections of a measurement object in which the projections are used to create images of the measurement object, which has the following steps:

specifying a set-point value for a factor that is characteristic of the quality of the projections to be produced by the computed tomography scanner;

sequentially producing projections of the measurement object, by determining an actual value of the factor that is characteristic of the quality of the particular projection produced by the computed tomography scanner between the productions of successive projections and by regulating the primary intensity of an X-ray source of the computed tomography scanner between the productions of successive projections such that the actual value for the characteristic factor of each of the projections produced by the computed tomography scanner is kept at the specified set-point value.

Thus according to the present invention, the primary intensity of an X-ray source of a computed tomography scanner between the productions of successive projections (and thus in quasi-real time) is regulated in such a way that the actual value of the factor that is characteristic of the quality of the projections to be produced by the computed tomography scanner is kept constant at the specified set-point value in the projections produced by the computed tomography scanner. Consequently, the primary intensity required for producing the projections is just as high as is precisely necessary for the desired quality of the projections (and thus for the images to be generated from the projections).

Since the primary intensity required for a specified quality of the projections and thus of the images is at the same time also always the minimal primary intensity required to produce projections and hence images with the specified quality, it is possible with the method of the invention to minimize the X-ray dose of a patient without lessening the quality of the images to be generated from the projections.

Also by means of the method of the invention, the ease of use for the user of the computed tomography scanner is enhanced, since by specifying the desired set-point value for the factor that is characteristic of the quality of the projections to be produced by the computed tomography scanner, in contrast to specifying a primary intensity of the X-ray source directly, can vary the variable that is relevant for him (that is, the quality of the images to be produced by means of the computed tomography scanner).

In order to free a user of the computed tomography scanner from having to input what for him might be an abstract and hence hard to estimate a set-point value for the factor characteristic of the quality of the projections to be produced by the computed tomography scanner, it is especially advantageous if the step of specifying the set-point value for the factor characteristic of the quality of the projections to be produced by the computed tomography scanner has the following subsidiary steps:

specification, by a user of the computed tomography scanner before the projections are produced, of a quality request or demand pertaining to the images to be generated by the computed tomography scanner from the projections to be produced;

conversion of the specified quality request into the set-point value for the factor that is characteristic of the quality of the projections to be produced by the computed tomography scanner.

It is thus possible for the user, by simply specifying a quality request (such as high, low, medium), to set a corresponding set-point value for the factor that is characteristic of the quality of the projections to be produced by the computed tomography scanner.

In general it is advantageous if the step of producing a projection of the measurement object includes the emission of an X-ray beam having the primary intensity by an X-ray source of the computed tomography scanner, and measuring a distribution of intensity values of a received X-ray beam by means of a receiving unit.

In a first embodiment of the method of the invention the factor that is characteristic of the quality of the projections to be produced by the computed tomography scanner is the relative noise of the distribution of the intensity values of the respective projection.

However, it is especially advantageous if, in an alternative second embodiment of the method of the invention, the factor that is characteristic of the quality of the projections to be produced by the computed tomography scanner is the relative noise of a distribution of the attenuation values the respective projection, and the attenuation values S of the respective projection are calculated from the measured intensity values I of the respective projection and the primary intensity $I_0$, used to produce the respective projection, by the following formula:

$$S = \ln(I_0/I)$$

Since the relative noise of the attenuation value of an X-ray beam measured by the computed tomography scanner has a decisive influence on the quality of the projections obtained from the measured X-ray beam and thus of the images generated from the projections, the relative noise of the attenuation value is a very well-suited indicator for the quality of the images to be obtained by means of the computed tomography scanner.

In the second embodiment, it is furthermore especially advantageous if the regulation of the primary intensity $I_0$ of the X-ray source of the computed tomography scanner between the production of successive projections is effected, on the basis of a set-point value $\sigma_{set\text{-}point}$ for the relative noise of the distribution of the attenuation values, by an intensity ratio $$v = I/I_0$$

of the measured intensity values I of the received X-ray beam to the primary intensity $I_0$ of the X-ray source, and a constant $\delta$, by the formula $$I_0 = \frac{1}{v \cdot \sigma_{set\text{-}point}^2 \cdot \ln^2[(1/v) + \delta]}$$

where $\delta$ is a small positive number unequal to zero, so as to avoid an expression "ln(0)" that is mathematically not allowed.

As a result, regulating the primary intensity can be done in an especially simple way.

The method according to the invention for controlling a computed tomography scanner can, because of the attainable low primary intensity of the X-ray beam to be emitted by the X-ray source, and the attendant low X-ray dosage to the measurement object (such as a patient) being observed, be used preferably in the field of early diagnosis or for full-body scans.

It is also especially advantageous if before the projections are produced, a suitable starting value (i.e. an initial or outset value) for the primary intensity of the X-ray source of the computed tomography scanner is estimated on the basis of the specified set-point value for the factor that is characteristic of the quality of the projections to be produced by the computed tomography scanner.

As a result, obtaining a first projection to be produced by the computed tomography scanner using an unnecessarily high primary intensity of the X-ray beam emitted by the radiation source, thus exposing a measurement object under observation to an unnecessarily high radiation dose, can be avoided.

Preferably, the set-point value for the factor that is characteristic of quality of the projections to be produced by the computed tomography scanner is manually specified by a user of the computed tomography scanner before the projections are produced.

As a result, a good adaptation of the computed tomography scanner can be made by the user to a measurement object under observation or to a desired measurement method.

The object is also attained by a computed tomography scanner, which has an X-ray source for emitting an X-ray beam at a primary intensity, a receiving unit for receiving the X-ray beam emitted by the X-ray source, and a regulating device (which may involve either an open or a closed-loop control) for controlling the primary intensity of the X-ray beam emitted by the X-ray source; the regulating device is embodied in order to calculate, from the X-ray beam received by the receiving unit in the production of a projection, an actual value in quasi-real time for a factor that is characteristic of the quality of the projection produced by the computed tomography scanner; and this regulating device is also embodied in order to regulate the primary intensity of the X-ray source of the computed tomography scanner, for producing the respective next projection, in such a way that for each of the individual projections, the actual value of the factor that is characteristic of the quality of the projections to be produced by the computed tomography scanner, is kept at a set-point value that is specified before the projections are produced.

Thus the method according to the invention can be performed by means of the computed tomography scanner according to the invention.

In a first preferred embodiment, the computed tomography scanner further has an input device, which is embodied for storage in memory by a user of the computed tomography scanner, before the projections are produced, of a manual input of the set-point value for the factor that is characteristic of the quality of the projections to be produced by the computed tomography scanner, and for specifying it to the regulating device.

If the computed tomography scanner has an input device, it is also especially advantageous if the input device is embodied in order to store in memory a manual input of a quality request from a user of the computed tomography scanner pertaining to the images to be generated by the computed tomography scanner from the projections to be produced before the projections are produced, and is also embodied in order to perform a conversion of the specified quality request to the set-point value for the factor that is characteristic of the quality of the projections to be produced by the computed tomography scanner and to specify the thus-obtained set-point value to the regulating device.

Because of the provision of an input device embodied in this way, it is possible for a user of the computed tomography scanner of the invention to perform an adaptation of the computed tomography scanner to a measurement object under observation or to a desired measuring method.

It is furthermore advantageous if the factor that is characteristic of the quality of the projections to be produced by the computed tomography scanner is the relative noise of a distribution, measured by the receiving unit, of intensity values of the X-ray beam emitted by the X-ray source for producing the respective projection and received by the receiving unit.

In an especially preferred embodiment, however, the factor that is characteristic of the quality of the projections to be produced by the computed tomography scanner is the relative noise of a distribution of attenuation values of the respective projection.

Preferably, the regulating device is embodied in order to regulate the primary intensity $I_0$ of the X-ray source of the computed tomography scanner, between the productions of successive projections, on the basis of a set-point value $\sigma_{set-point}$ for the relative noise of the distribution of the attenuation values, an intensity ratio $$v = I/I_0$$

of the measured intensity values I of the received X-ray beam, to the primary intensity $I_0$ of the X-ray source, and a constant $\delta$, by the formula $$I_0 = \frac{1}{v \cdot \sigma_{set-point}^2 \cdot \ln^2[(1/v) + \delta]}$$

where $\delta$ is a small positive number unequal to zero, for avoiding ln(0).

Since to produce projections of a measurement object with a specified quality and thus for generating images from the projections, only an X-ray beam of minimal primary intensity must be emitted by the X-ray source, and the X-ray dosage to a measurement object under observation, in particular a patient, is consequently especially low, it is especially advantageous if the computed tomography scanner is embodied for use in the field of early diagnosis or for full-body scans.

In an especially preferred embodiment, the regulating device is further embodied in order before the projections are produced, on the basis of the specified set-point value for the factor that is characteristic of the quality of the projections to be produced by the computed tomography scanner, a suitable starting value for the primary intensity of the X-ray source (1) of the computed tomography scanner to estimate a suitable starting value.

If an input device is provided, then it is furthermore advantageous if the input device includes a memory device, in which many set-point values for the factor that is characteristic of the quality of the projections to be produced by the computed tomography scanner are stored in memory, and the set-point values are associated with various measuring methods of the computed tomography scanner and thus with various quality requests made by a user of the computed tomography scanner of the images to be generated by the computed tomography scanner from the projections to be produced.

This enables automatic association of a quality request from a user with a set-point value for the factor that is characteristic of the quality of the projections to be produced by the computed tomography scanner and thus enhances the ease of use of the computed tomography scanner of the invention.

A preferred embodiment of the present invention will be described in further detail below in conjunction with the drawings. Shown are FIG. 1, a flow chart of an especially preferred embodiment of the method of the invention.

Figure 2:
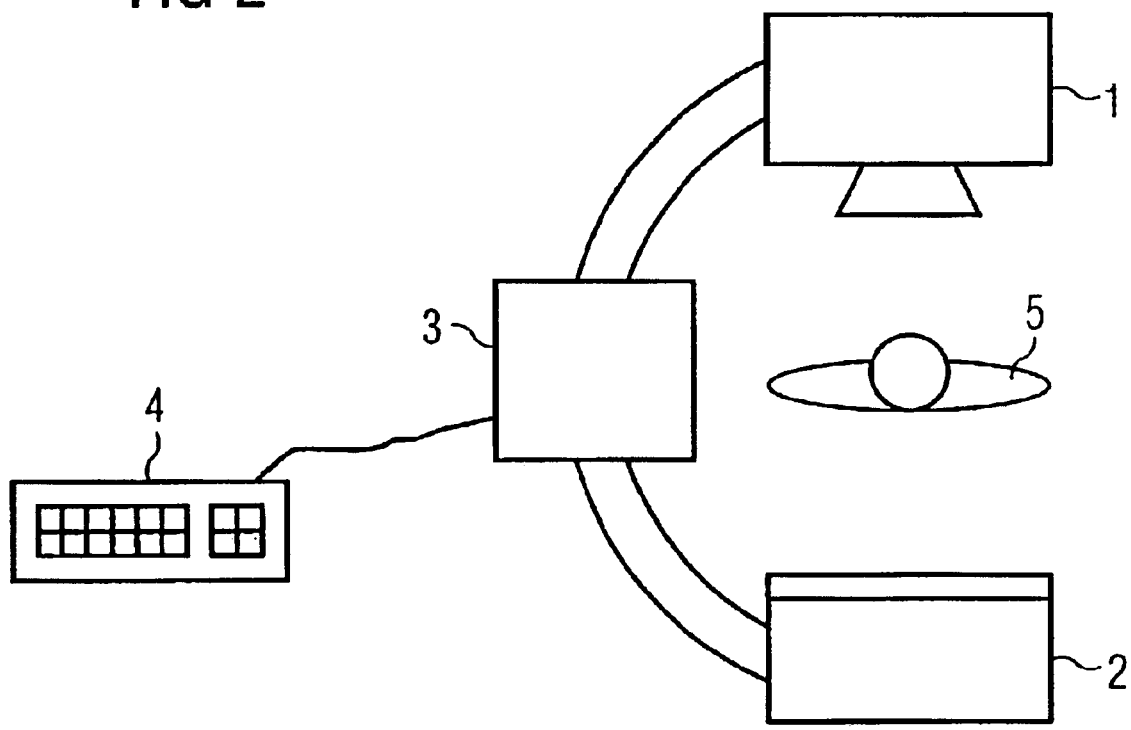

FIG. 2, schematically, a computed tomography scanner that is suitable for performing the method of the invention.

In conjunction with FIG. 1, a preferred embodiment of the method of the invention, which can be performed by the computed tomography scanner of the invention shown in FIG. 2, will be described below.

To that end, the computed tomography scanner shown schematically in FIG. 2 has an X-ray source 1 for emitting an X-ray beam at a primary intensity $I_0$, a receiving unit 2 for receiving the X-ray beam emitted by the X-ray source 1, and a regulating device 3 for controlling the primary intensity $I_0$ of the X-ray beam emitted by the X-ray source 1. An input device 4 is also connected to the regulating device 3 and serves as an interface with a user of the computed tomography scanner of the invention.

As can be seen from FIG. 1, in a first step S1 in the method of the invention, a set-point value $\sigma_{set-point}$ is specified for a factor $\sigma(I)$ that is characteristic of the quality of the projections to be produced by the computed tomography scanner.

According to this particularly preferred embodiment, the specification, by a user of the computed tomography scanner of the invention, of the set-point value $\sigma_{set-point}$ is effected via the input device 4, by manual specification of a quality request A for the images to be generated by the computed tomography scanner from the projections to be produced. This quality request can for instance be a requirement in terms of the resolution of the images to be generated (very low resolution, low resolution, normal resolution, high resolution, very high resolution], or the specification of a measuring method (full-body scan, detail scan, etc.). The specified quality request A is stored in memory in the input device 4.

Next, by means of the input device 4, a conversion of the specified quality request A into the set-point value $\sigma_{set-point}$ is effected, for the factor $\sigma(I)$ that is characteristic of the quality of the projections to be produced by the computed tomography scanner. For that purpose, the input device 4 includes a memory device, in which many set-point values $\sigma_{set-point}$ are stored in memory for the factor $\sigma(I)$ characteristic of the quality of the projections to be produced by the computed tomography scanner. The set-point values $\sigma_{set-point}$ stored in memory in the input device 4 are associated with various measuring methods of the computed tomography scanner and hence various quality requests A from the user of the computed tomography scanner with regard to the images to be generated by the computed tomography scanner from the projections to be produced. As a result of this association, it is possible for the user-specified quality request to be converted in a simple way into the factor $\sigma(I)$ that is characteristic of the quality of the projections to be produced by the computed tomography scanner.

The set-point value $\sigma_{set-point}$ thus obtained is then specified to the regulating device 3 of the computed tomography scanner of the invention.

In the preferred embodiment shown, the thus-obtained set-point value $\sigma_{set-point}$ for the factor $\sigma(I)$ characteristic of the quality of the projections to be produced by the computed tomography scanner is a maximum value for the relative noise $\sigma_{rel}(S)$ of a distribution of attenuation values S of the particular projection to be produced by the computed tomography scanner.

The attenuation values S of the particular projection are calculated from the measured intensity values I of the respective projection and from the primary intensity $I_0$ used to produce the respective projection, in accordance with the following formula:

$$S=ln(I_0/I)$$

Alternatively, however, it is possible also to use the relative noise $\sigma_{rel}(I)$ of a distribution of intensity values I of the particular projection to be produced by the computed tomography scanner directly as the factor $\sigma(I)$ that is characteristic of the quality of the projections to be produced by the computed tomography scanner.

In a subsequent step S2, the regulating device 3 of the computed tomography scanner of the invention, on the basis of the specified set-point value $\sigma_{set-point}$ for the factor $\sigma_{rel}(S)$ characteristic of the quality of the projections to be produced by the computed tomography scanner, estimates a suitable starting value $I_{0Start}$ for the primary intensity $I_0$ of the X-ray beam to be emitted by the X-ray source 1 of the computed tomography scanner. As a result, it can be presented that the X-ray source 1 of the computed tomography scanner of the invention, in producing a first image of a measurement object 5 under observation, will produce X-radiation at an unnecessarily high primary intensity.

In the next step S3, using the starting value $I_{0start}$ estimated by the regulating device 3 for the primary intensity $I_0$ of the X-ray beam emitted by the X-ray source 1, a first projection of the measurement object 5 under observation is produced. In this operation, the X-ray beam emitted by the X-ray source 1, after passing through the measurement object 5, such as a patient, is received by the receiving unit 2. The receiving unit 2, in the present example, measures a distribution of intensity values I of the X-ray beam received.

Next, in step S4, the regulating device 3 determines an actual value, in the projection produced by the computed tomography scanner, for the factor $\sigma_{rel}(S)$ that is characteristic of the quality of the projection produced.

In the embodiment shown, for this purpose the regulating device 3 determines the relative noise $\sigma_{rel}(S)$ of the distribution of the attenuation values S in the projection produced by the computed tomography scanner. Naturally, the factor characteristic of the quality of the projection produced can alternatively for instance be the relative noise $\sigma_{rel}(I)$ of the distribution of then intensity values I in the projection produced by the computed tomography scanner, or some other suitable factor.

In the following step S5, the regulating device 3 regulates the primary intensity $I_0$ of the X-ray source 1 of the computed tomography scanner in such a way that the actual value of the characteristic factor $\sigma_{rel}(S)$ of the projection produced by the computed tomography scanner is kept at the specified set-point value $\sigma_{set-point}$.

In the particularly preferred embodiment described here, the regulating device 3 is embodied such that between the productions of successive projections (and thus in quasi-real time), on the basis of the specified set-point value for the relative noise $\sigma_{set-point}$ of the distribution of the attenuation values S, an intensity ratio $$v=I/I_0$$

of the intensity values I, measured by the receiving unit 2, of the X-ray beam, it regulates the primary intensity $I_0$ of the X-ray source 1 of the computed tomography scanner to the primary intensity $I_0$ of the X-ray source 1 and a constant δ, in accordance with the following formula:

$$I_0 = \frac{1}{\nu \cdot \sigma_{set\text{-}point}^2 \cdot \ln^2[(1/\nu) + \delta]}$$

The symbol δ stands for a small positive number not equal to zero, so as to avoid an expression "ln(0)" that is mathematically not allowed.

Now, in step S6, the question is asked whether all the projections to be produced have been produced. If so, the method of the invention ends.

If that is not the case, then in step S7 a further projection of the measurement object 5 under observation is produced, using the primary intensity $I_0$, newly regulated in step S5, for the X-ray beam to be emitted by the X-ray source 1 of the computed tomography scanner of the invention.

The method then continues with step S4 and once again determines the actual value for the factor $\sigma_{rel}(S)$ characteristic of the quality of the projection produced (that is, in the present embodiment, the relative noise $\sigma_{rel}(S)$ of the distribution of the attenuation values S in the further projection produced by the computed tomography scanner of the invention).

This loop comprising steps S4, S5, S6 and S7, is executed until such time as it is decided in step S6 that all the projections to be produced have been produced.

In summary, in the method of the invention and the computed tomography scanner of the invention, the primary intensity of the X-ray beam emitted by the X-ray source, employed for producing projections (and thus for generating images from the projections) with a specified quality, is always precisely as high as needed at exactly that time. This can be ascribed to the fact that the primary intensity of the X-ray beam, during the production of the projections, is regulated in quasi-real time (between the productions of successive projections) by the input device, in such a way that an actual value for a factor characteristic of the quality of the projections to be produced, is kept constant, in the projections produced by the computed tomography scanner, at a set-point value that is specified before the projections are produced.

Within the scope of this invention, the term "quasi-real time" is intended to mean a procedure which either functions continuously, or is at such a fast pace (i.e. such a high speed or is clocked so fast) that it is terminated in good time before the next method step.

Since the primary intensity required for a specified quality of the projections (and hence of the images to be generated from the projections) is at the same time also always the minimum primary intensity for producing projections with the specified quality, it is possible with the method and the computed tomography scanner of the invention to minimize the X-radiation dose of a measurement object, in particular a patient, without sacrifices in quality. Moreover, by means of the method of the invention, the ease of use for a user of the computed tomography scanner of the invention is enhanced, since in contrast to specifying a primary intensity of the X-ray source, the user, by specifying a desired quality, can directly influence the variable that is relevant for him.

Consequently, with the method and the computed tomography scanner of the invention, it is also possible to produce projections with a defined low quality. This allows the method of the invention and the computed tomography scanner of the invention also to be used in the field of early diagnosis or for full-body scans.

What is claimed is:

1. A method for controlling a computed tomography scanner for producing projections of a measurement object, in which the projections are used to create images of the measurement object, comprising:

specifying a set-point value ($\sigma_{set\text{-}point}$) for a factor ($\sigma(I)$) that is characteristic of a quality of the projections to be produced by the computed tomography scanner;

determining an actual value of the factor ($\sigma(I)$) that is characteristic of the quality of the particular projection produced by the computed tomography scanner between the productions of successive projections; and regulating a primary intensity ($I_0$) of an X-ray source of the computed tomography scanner, between the productions of successive projections, such that the actual value for the characteristic factor ($\sigma(I)$) of each of the projections produced by the computed tomography scanner is kept at about the specified set-point value ($\sigma_{set\text{-}point}$).

2. The method of claim 1, wherein the act of specifying the set-point value ($\sigma_{set\text{-}point}$) further comprises:

specifying, by a user of the computed tomography scanner before the projections are produced, a quality request A pertaining to the images to be generated by the computed tomography scanner from the projections to be produced; and converting the specified quality request A into the set-point value ($\sigma_{set\text{-}point}$) for the factor ($\sigma(I)$) that is characteristic of the quality of the projections to be produced by the computed tomography scanner.

3. The method of claim 1 wherein the projections of the measurement object are produced sequentially.

4. The method of claim 1, further comprising producing an emission of an X-ray beam having a primary intensity ($I_0$) by an X-ray source of the computed tomography scanner, and measuring a distribution of intensity values (I) of a received X-ray beam by means of a receiving unit.

5. The method of claim 1, wherein the factor ($\sigma(I)$) that is characteristic of the quality of the projections to be produced by the computed tomography scanner is a relative noise ($\sigma_{rel}(I)$) of the distribution of the intensity values (I) of the respective projection.

6. The method of claim 4, wherein the factor ($\sigma(I)$) is a relative noise ($\sigma_{rel}(I)$) of a distribution of attenuation values (S) of the respective projection, and the attenuation values S of the respective projection are calculated from the measured intensity values I of the respective projection and the primary intensity $I_0$, used to produce the respective projection, by the following formula:

$$S = ln(I_0/I).$$

7. The method of claim 6, wherein a regulation of the primary intensity $I_0$ of the X-ray source of the computed tomography scanner is effected between the productions of successive projections on the basis of a set-point value $\sigma_{set\text{-}point}$ for the relative noise ($\sigma_{rel}(S)$) of the distribution of the attenuation values (S), an intensity ratio $\nu = I/I_0$ of the measured intensity values I of the received X-ray beam to the primary intensity $I_0$ of the X-ray source (1), and a constant δ, by the formula $$I_0 = \frac{1}{\nu \cdot \sigma_{set\text{-}point}^2 \cdot \ln^2[(1/\nu) + \delta]}$$

where δ is a small positive number unequal to zero.

8. The method of claim 1, wherein the method is utilized in the field of early diagnosis or for full-body scans.

9. The method of claim 1, wherein before the projections are produced, a suitable starting value ($I_{0start}$) for the primary intensity ($I_0$) of the X-ray source (1) of the computed tomography scanner is estimated on the basis of the specified set-point value ($\sigma_{set\ point}$) for the factor ($\sigma(I)$).

10. The method of claim 1, wherein the set-point value ($\sigma_{set-point}$) for the factor ($\sigma(I)$) is manually specified by a user of the computed tomography scanner before the projections are produced.

11. The method of claim 1, wherein before the projections are produced, a suitable starting value ($I_{0start}$) for the primary intensity ($I_0$) of the X-ray source (1) of the computed tomography scanner is estimated on the basis of the specified set-point value ($\sigma_{set-point}$) for the factor ($\sigma(I)$) and wherein the set-point value ($\sigma_{set-point}$) for the factor ($\sigma(I)$) is manually specified by a user of the computed tomography scanner before the projections are produced.

12. A computed tomography scanner, having an X-ray source for emitting an X-ray beam at a primary intensity ($I_0$), a receiving unit for receiving the X-ray beam emitted by the X-ray source, and a regulating device for controlling the primary intensity ($I_0$) of the X-ray beam emitted by the X-ray source, and wherein the regulating device is embodied for:

calculating, from the X-ray beam received by the receiving unit in the production of a projection, an actual value in quasi-real time for a factor ($\sigma(I)$) that is characteristic of the quality of the projection produced by the computed tomography scanner; and regulating the primary intensity ($I_0$) of the X-ray source of the computed tomography scanner, for producing the respective next projection, in such a way that for each of the individual projections, the actual value of the factor ($\sigma(I)$) that is characteristic of the quality of the projections to be produced by the computed tomography scanner, is substantially kept at a set-point value ($\sigma_{set-point}$) that is specified before the projections are produced.

13. The computed tomography scanner of claim 12, further comprising an input device which is embodied for storing in memory by a user of the computed tomography scanner, before the projections are produced, a manual input of the set-point value ($\sigma_{set-point}$) for the factor ($\sigma(I)$), and for specifying the set-point value ($\sigma_{set-point}$) to the regulating device.

14. The computed tomography scanner of claim 13, wherein the input device is used for:

storing in memory a manual input of a quality request A from a user of the computed tomography scanner pertaining to the images to be generated by the computed tomography scanner from the projections to be produced before the projections are produced; and performing a conversion of the specified quality request A to the set-point value ($\sigma_{set-point}$) for the factor ($\sigma(I)$) that is characteristic of the quality of the projections to be produced by the computed tomography scanner and to specify the set-point value ($\sigma_{set-point}$) to the regulating device.

15. The computed tomography scanner of claim 12, wherein the factor ($\sigma(I)$) is a relative noise ($\sigma_{rel}(I)$) of a distribution, measured by the receiving unit, of intensity values (I) of the X-ray beam emitted by the X-ray source for producing the respective projection and received by the receiving unit.

16. The computed tomography scanner of claim 12, wherein the factor ($\sigma(I)$) is a relative noise ($\sigma_{rel}(S)$) of a distribution of attenuation values (S) of the respective projection.

17. The computed tomography scanner of claim 16, wherein the regulating device is embodied in order to regulate the primary intensity $I_0$ of the X-ray source of the computed tomography scanner, between the productions of successive projections, on the basis of a set-point value $\sigma_{set-point}$ for the relative noise ($\sigma_{rel}(S)$) of the distribution of the attenuation values (S), an intensity ratio $v=I/I_0$ of the measured intensity values I of the received X-ray beam, to the primary intensity $I_0$ of the X-ray source, and a constant $\delta$, by the formula $$I_0 = \frac{1}{v \cdot \sigma_{set-point}^2 \cdot \ln^2[(1/v) + \delta]}$$

where $\delta$ is a small positive number unequal to zero.

18. The computed tomography scanner of claim 12 wherein the scanner is utilized in a field from the group of: early diagnosis and for full-body scans.

19. The computed tomography scanner of claim 12, wherein the regulating device is further embodied in order before the projections are produced, on the basis of the specified set-point value ($\sigma_{set-point}$) for the factor ($\sigma(I)$) that is characteristic of the quality of the projections to be produced by the computed tomography scanner, a suitable starting value ($I_{0start}$) for the primary intensity ($I_0$) of the X-ray source of the computed tomography scanner to estimate a suitable starting value ($I_{0start}$).

20. The computed tomography scanner of claim 17, wherein the regulating device is further embodied in order before the projections are produced, on the basis of the specified set-point value ($\sigma_{set-point}$) for the factor ($\sigma(I)$) that is characteristic of the quality of the projections to be produced by the computed tomography scanner, a suitable starting value ($I_{0start}$) for the primary intensity ($I_0$) of the X-ray source of the computed tomography scanner to estimate a suitable starting value ($I_{0start}$).

21. The computed tomography scanner of claim 13, wherein the input device includes a memory device, in which many set-point values ($\sigma_{set-point}$) for the factor ($\sigma(I)$) are stored in memory, and the set-point values (($\sigma_{set-point}$) are associated with various measuring methods of the computed tomography scanner and thus with various quality requests A made by a user of the computed tomography scanner of the images to be generated by the computed tomography scanner from the projections to be produced.

22. The computed tomography scanner of claim 14, wherein the input device includes a memory device, in which many set-point values ($\sigma_{set-point}$) for the factor ($\sigma(I)$) are stored in memory, and the set-point values ($\sigma_{set-point}$) are associated with various measuring methods of the computed tomography scanner and thus with various quality requests A made by a user of the computed tomography scanner of the images to be generated by the computed tomography scanner from the projections to be produced.

* * * * *